United States Patent
Lin et al.

(10) Patent No.: US 8,755,045 B2
(45) Date of Patent: Jun. 17, 2014

(54) DETECTING METHOD FOR FORMING SEMICONDUCTOR DEVICE

(75) Inventors: Jyuh-Fuh Lin, Chunan Township, Miaoli County (TW); Te-Chih Huang, Chu-Bei (TW); Guo-Tsai Huang, Hsinchu County (TW); Jia-Rui Hu, Taichung (TW); Chih-Ming Ke, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 334 days.

(21) Appl. No.: 13/344,670

(22) Filed: Jan. 6, 2012

(65) Prior Publication Data

US 2013/0176558 A1 Jul. 11, 2013

(51) Int. Cl.
*G01N 21/00* (2006.01)
(52) U.S. Cl.
USPC .................. 356/237.5; 356/237.2; 356/237.3

(58) Field of Classification Search
USPC ............... 356/237.1–241.6, 242.1–243.8, 356/426–431, 600–640
See application file for complete search history.

(56) References Cited

U.S. PATENT DOCUMENTS

| | | | | |
|---|---|---|---|---|
| 5,892,578 A | * | 4/1999 | Suda | 356/123 |
| 6,763,141 B2 | * | 7/2004 | Xu et al. | 382/255 |
| 6,968,288 B2 | * | 11/2005 | Macaluso et al. | 702/155 |
| 7,685,558 B2 | * | 3/2010 | Lai et al. | 716/51 |
| 7,904,845 B2 | * | 3/2011 | Fouquet et al. | 716/136 |
| 8,572,518 B2 | * | 10/2013 | Tyminski et al. | 716/52 |

* cited by examiner

*Primary Examiner* — Gregory J Toatley
*Assistant Examiner* — Jarreas C Underwood
(74) *Attorney, Agent, or Firm* — Haynes and Boone, LLP

(57) ABSTRACT

In one embodiment, a method for detecting design defects is provided. The method includes receiving design data of an integrated circuit (IC) on a wafer, measuring wafer topography across the wafer to obtain topography data, calculating a scanner moving average from the topography data and the design data to provide a scanner defocus map across the wafer, and determining a hotspot design defect from the scanner defocus map. A computer readable storage medium, and a system for detecting design defects are also provided.

19 Claims, 10 Drawing Sheets

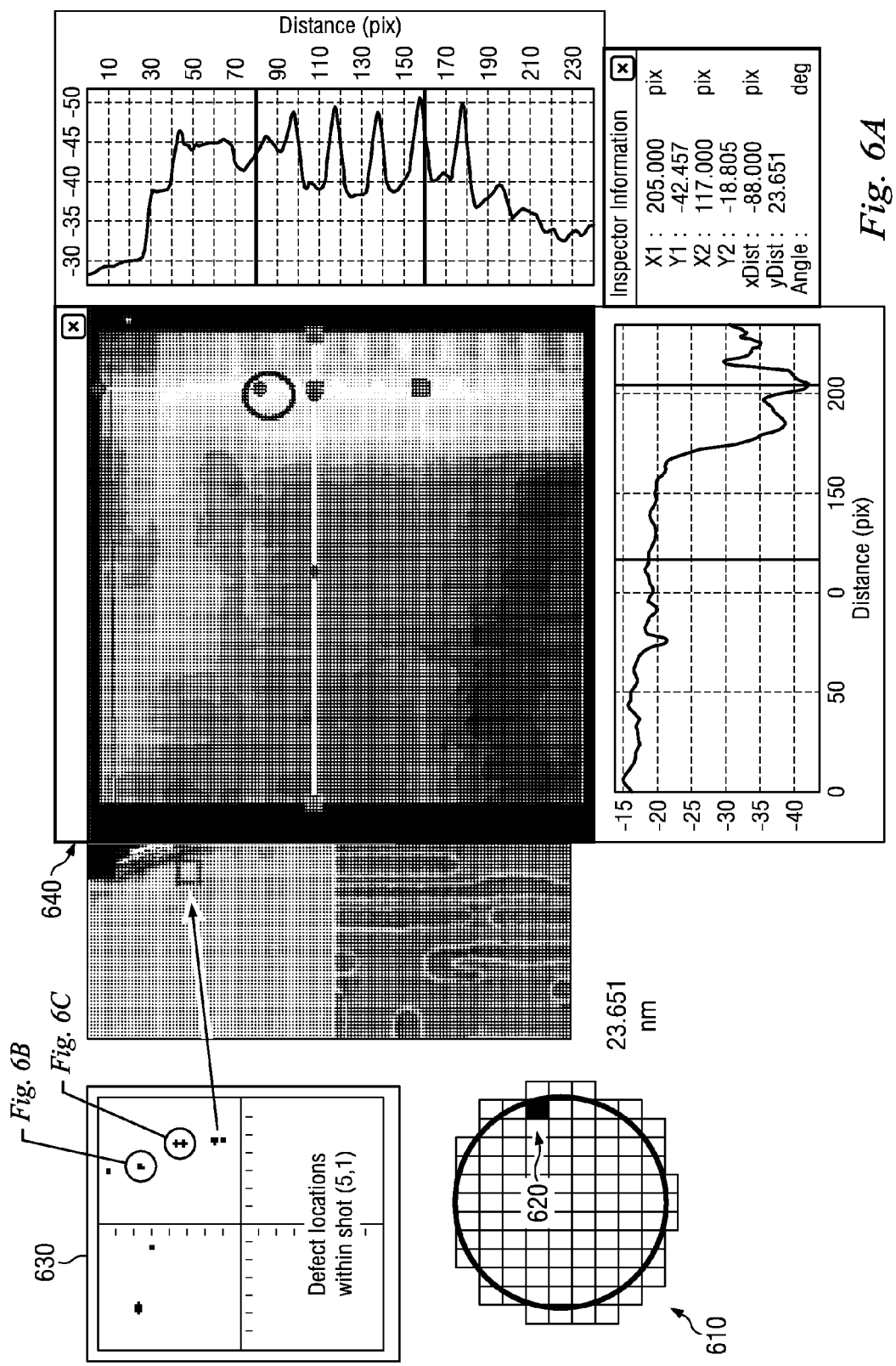

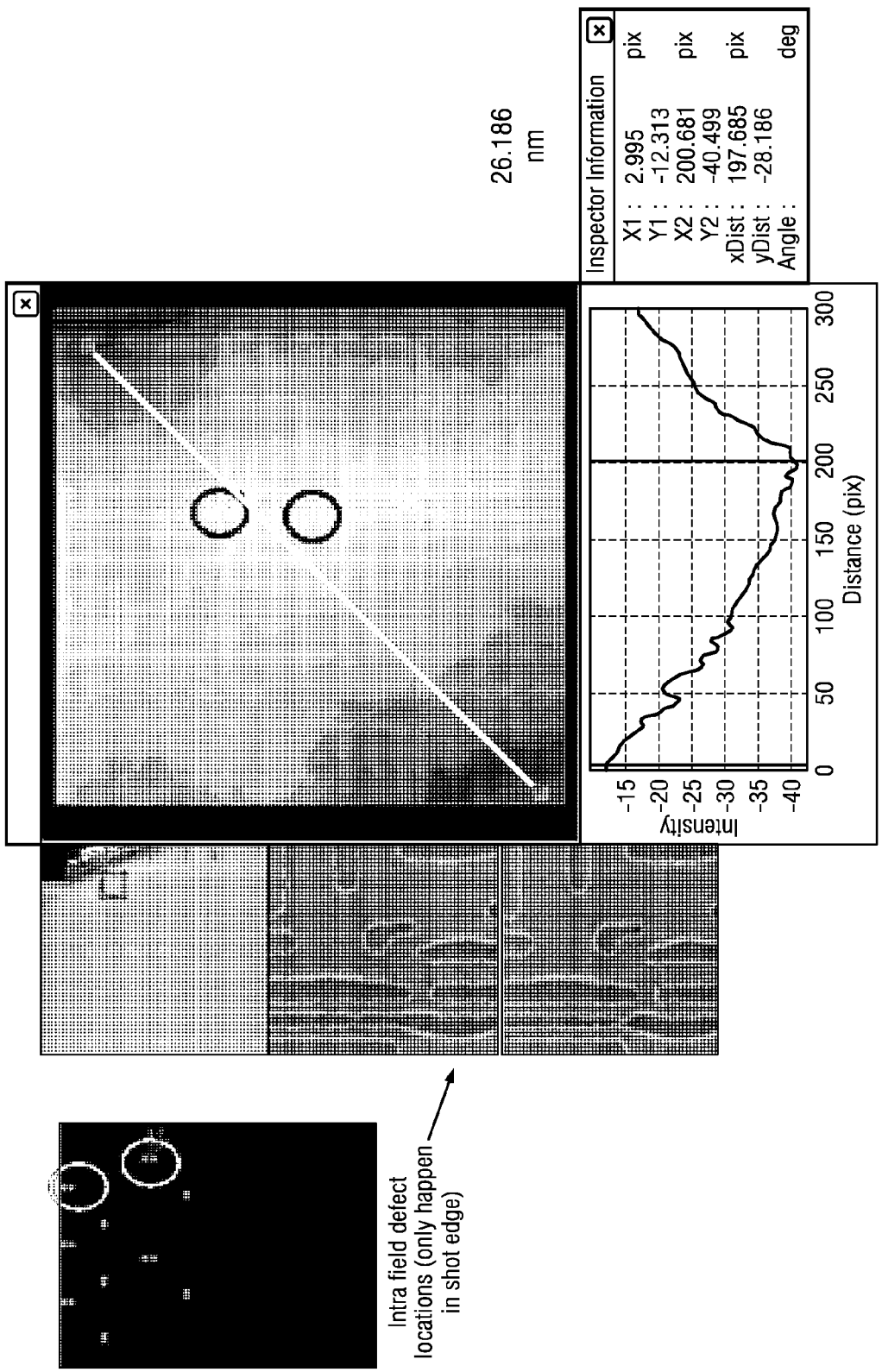

DETECTING METHOD FOR FORMING SEMICONDUCTOR DEVICE

BACKGROUND

Fabricating semiconductor devices, such as logic and memory devices, typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation.

Inspection processes are used at various steps during a semiconductor manufacturing process to detect defects on wafers or reticles to promote higher yield in the manufacturing process and thus higher profits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices. Furthermore, as design rules shrink, semiconductor manufacturing processes may be operating closer to the limitations on the performance capability of the processes, and smaller defects can have an impact on the electrical parameters of the device.

Detection methods of printability defects, such as those related to insufficient space and/or line width margins and which may also be referred to as hotspots, have traditionally not taken into consideration the wafer or chip topography.

Accordingly, it would be advantageous to develop improved and efficient computer-implemented methods, carrier media, and systems for detecting design defects.

SUMMARY

The present disclosure provides for many different embodiments. According to one embodiment, a method for detecting design defects is provided. The method includes receiving design data of an integrated circuit (IC) on a wafer, measuring wafer topography across the wafer to obtain topography data, calculating a scanner moving average from the topography data to provide a scanner defocus map across the wafer, and determining a hotspot design defect from the scanner defocus map and the design data.

In another embodiment, a computer readable storage medium is provided. The computer readable storage medium comprises computer readable instructions which when executed by a computer cause the computer to perform the operations of: receiving design data of an integrated circuit (IC) on a wafer; measuring wafer topography across the wafer to obtain topography data; calculating a scanner moving average from the topography data and the design data to provide a scanner defocus map across the wafer; and determining a hotspot design defect from the scanner defocus map.

In yet another embodiment, a system for detecting design defects is provided. The system includes an inspection tool configured to measure wafer topography across a wafer to obtain topography data, and a processor operably coupled to the inspection tool, the processor configured to perform the operations of: receiving design data of the IC on the wafer; calculating a scanner moving average from the topography data and the design data to provide a scanner defocus map across the wafer; and determining a hotspot design defect from the scanner defocus map.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
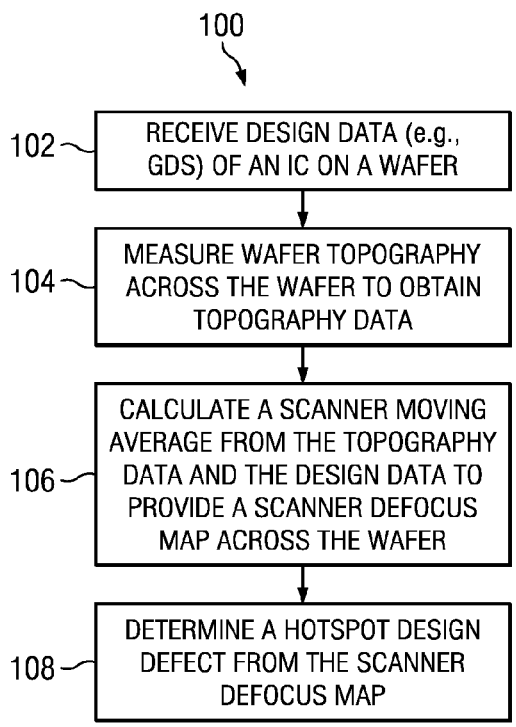
FIGS. 1 and 2 are flowcharts of methods for detecting design defects in accordance with embodiments of the present disclosure.

It is understood that the following disclosure provides many different embodiments, or examples, for implementing different features of the disclosure. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for the sake of simplicity and clarity. It is noted that the same or similar features may be similarly numbered herein for the sake of simplicity and clarity. In addition, some of the drawings may be simplified for clarity. Thus, the drawings may not depict all of the components of a given apparatus (e.g., device) or method.

Various aspects of the present disclosure will be described herein with reference to drawings that are schematic illustrations of idealized configurations of the present disclosure. As such, variations from the shapes of the illustrations as a result, for example, manufacturing techniques and/or tolerances, are to be expected. Thus, the various aspects of the present disclosure presented throughout this disclosure should not be construed as limited to the particular shapes of elements (e.g., regions, layers, sections, substrates, etc.) illustrated and described herein but are to include deviations in shapes that result, for example, from manufacturing. By way of example, an element illustrated or described as a rectangle may have rounded or curved features and/or a gradient concentration at its edges rather than a discrete change from one element to another. Thus, the elements illustrated in the drawings are schematic in nature and their shapes are not intended to illustrate the precise shape of an element and are not intended to limit the scope of the present disclosure.

It will be understood that when an element such as a region, layer, section, substrate, or the like, is referred to as being "on" another element, it can be directly on the other element or intervening elements may also be present. In contrast, when an element is referred to as being "directly on" another element, there are no intervening elements present. It will be further understood that when an element is referred to as being "formed" on another element, it can be grown, deposited, etched, attached, connected, coupled, or otherwise prepared or fabricated on the other element or an intervening element.

Furthermore, relative terms, such as "lower" or "bottom" and "upper" or "top", may be used herein to describe one element's relationship to another element as illustrated in the drawings. It will be understood that relative terms are intended to encompass different orientations of an apparatus in addition to the orientation depicted in the drawings. By way of example, if an apparatus in the drawings is turned over, elements described as being on the "lower" side of other elements would then be oriented on the "upper" sides of the other elements. The term "lower", can therefore, encompass both an orientation of "lower" and "upper", depending on the particular orientation of the apparatus. Similarly, if an apparatus in the drawing is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items It will be understood that although the terms "first" and "second" may be used herein to describe various regions, layers and/or sections, these regions, layers and/or sections should not be limited by these terms. These terms are only used to distinguish one region, layer or section from another region, layer or section. Thus, a first region, layer or section discussed below could be termed a second region, layer or section, and similarly, a second region, layer or section may be termed a first region, layer or section without departing from the teachings of the present disclosure.

It is understood that several processing steps and/or features of a device may be only briefly described, such steps and/or features being well known to those of ordinary skill in the art. Also, additional processing steps or features can be added, and certain of the following processing steps or features can be removed and/or changed while still implementing the claims. Thus, the following description should be understood to represent examples only, and are not intended to suggest that one or more steps or features is required.

Figure 2:
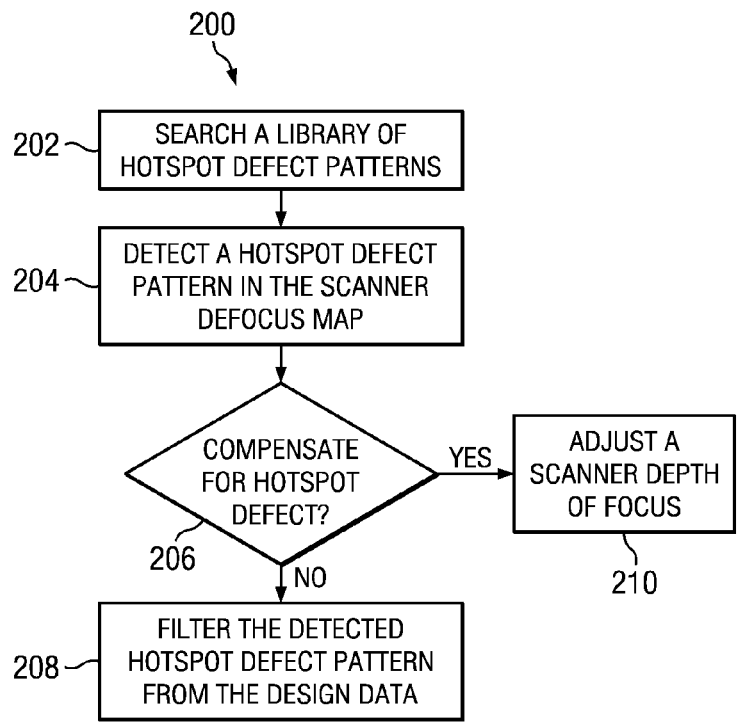
Figure 3:
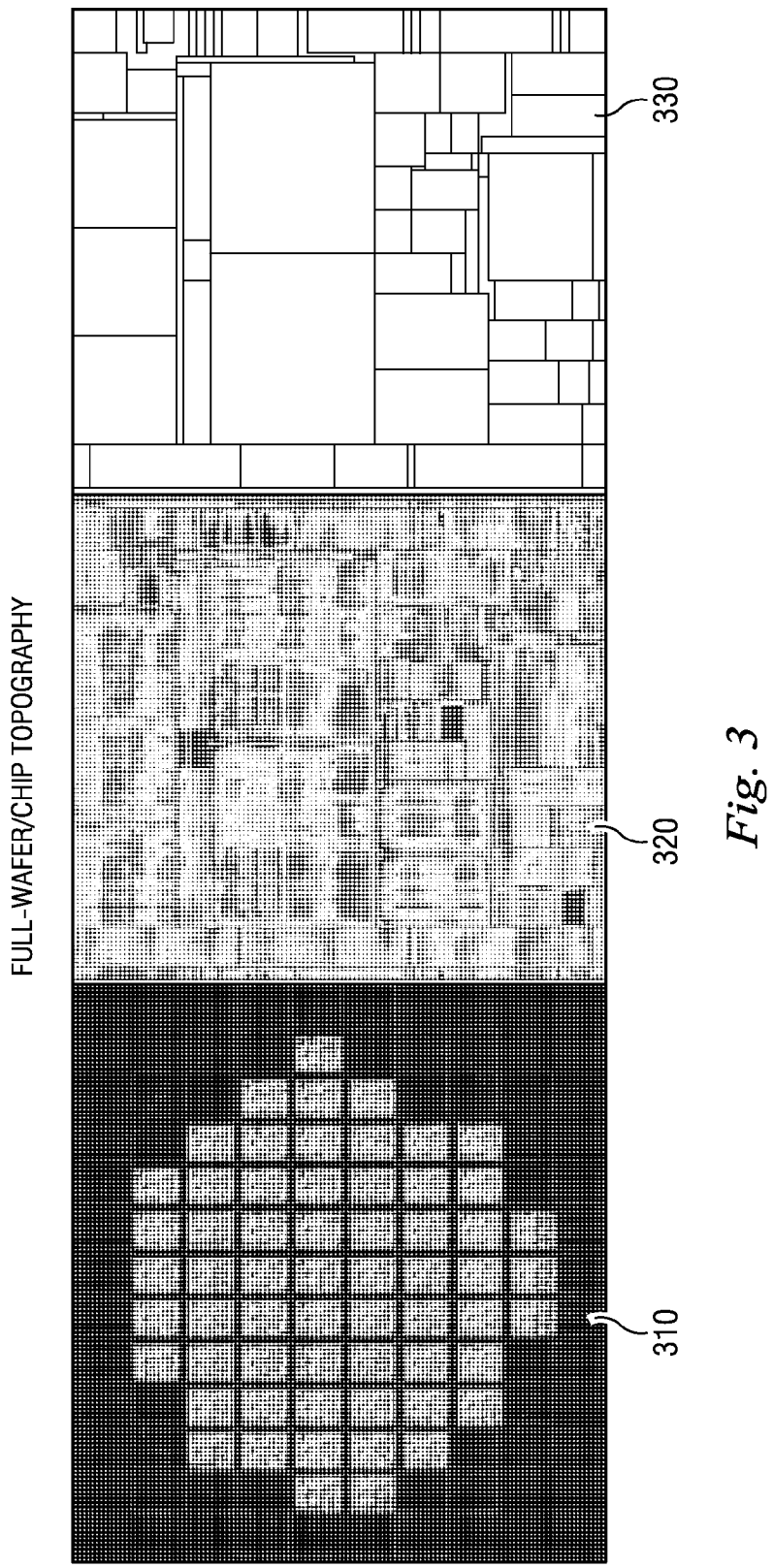
FIG. 3 illustrates measurement of the topography of a wafer and a chip and the provision of design data of the chip in accordance with an embodiment of the present disclosure.
Figure 4:
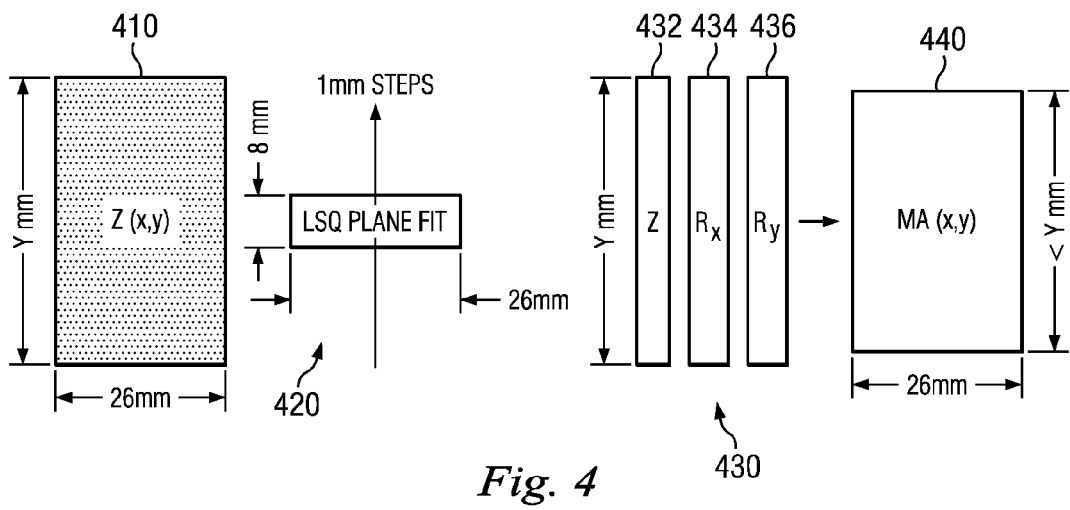
FIG. 4 illustrates calculation of a scanner moving average from topography data of the wafer in accordance with another embodiment of the present disclosure.
Figure 6:
FIG. 6 illustrates enlarged views and/or enhanced inspection of detected hotspot regions in accordance with embodiments of the present disclosure.
Figure 5:
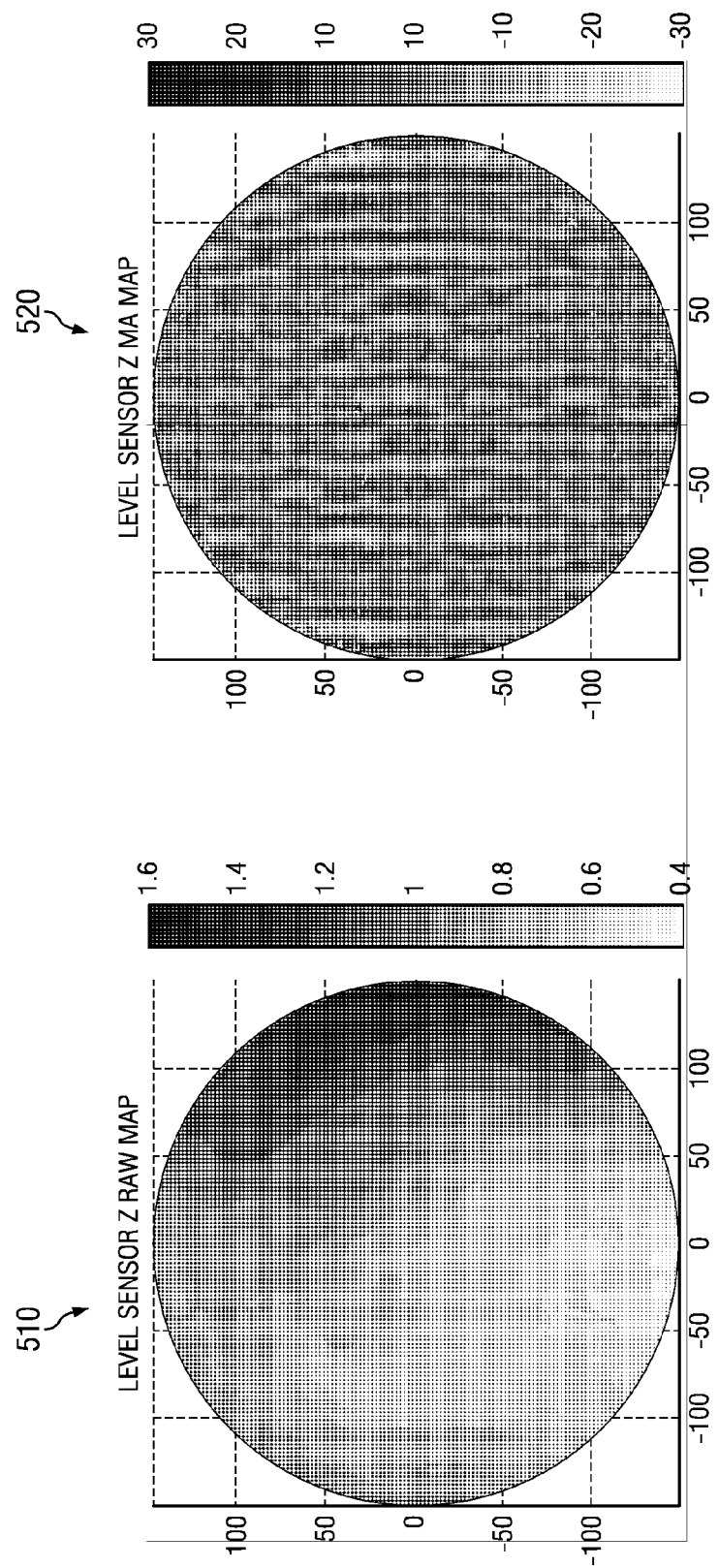
FIG. 5 illustrates a topography map across the wafer and a scanner defocus map across the wafer in accordance with embodiments of the present disclosure.
Figure 6B:
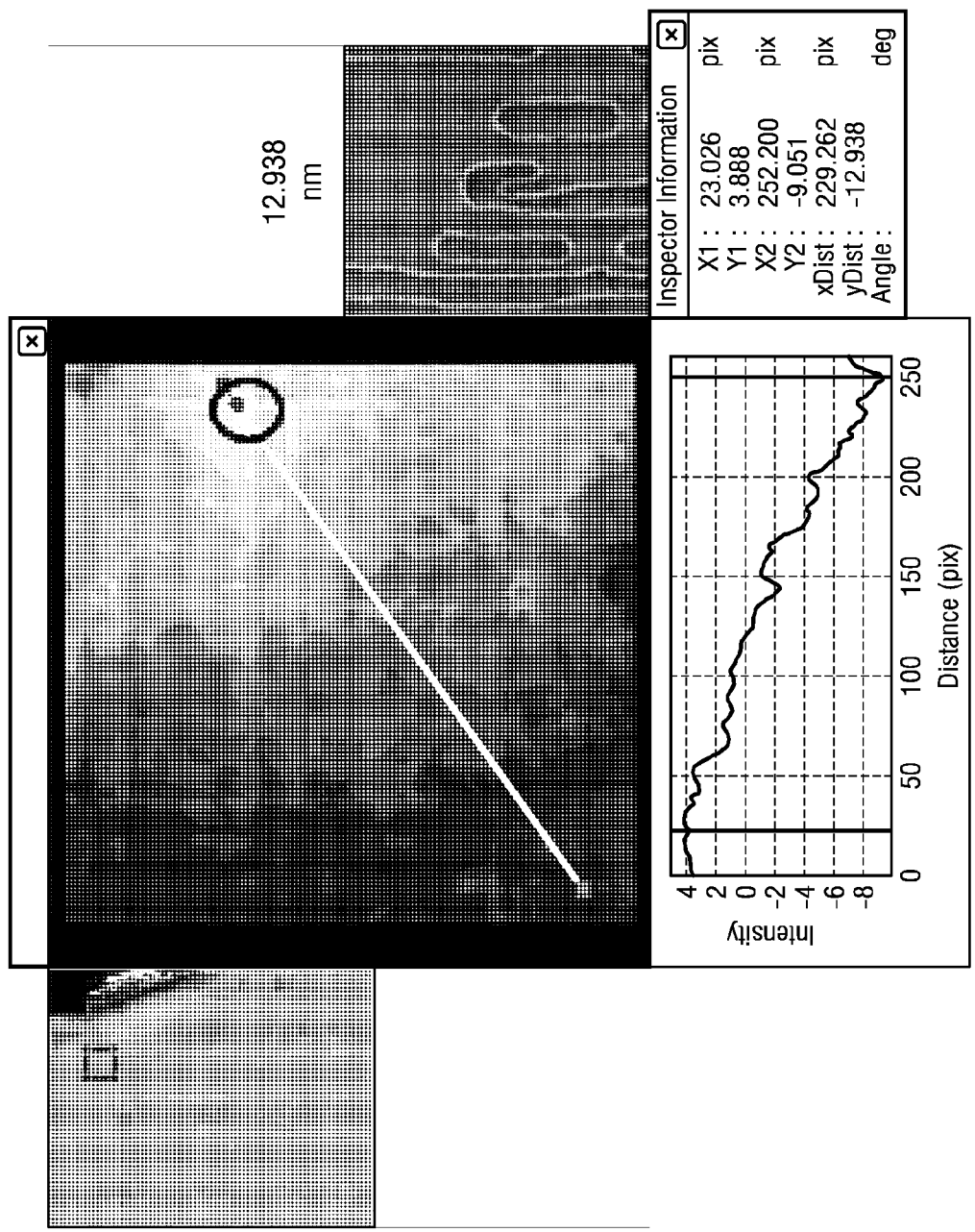
Figure 6D:
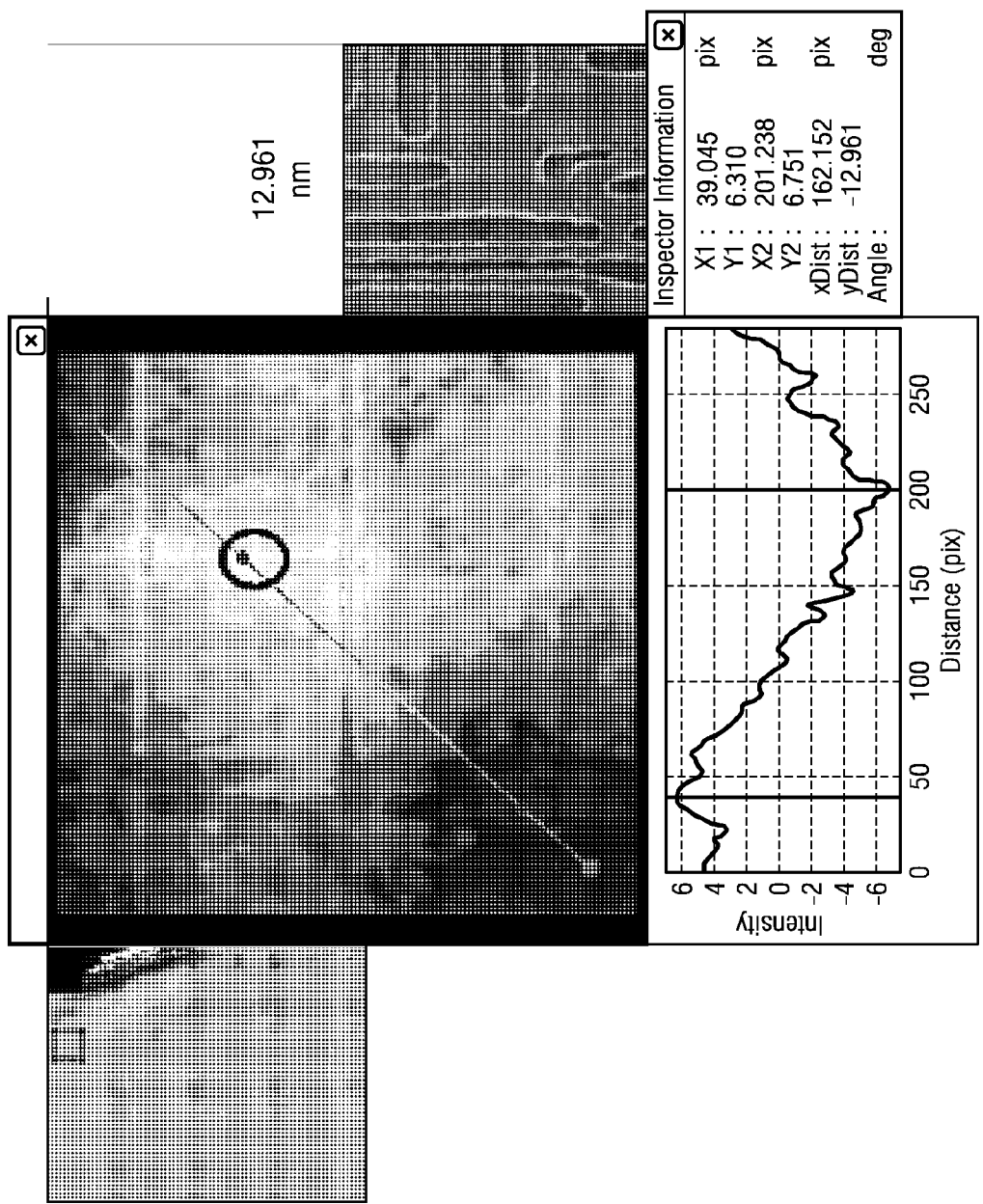

Referring now to the figures, FIGS. 1 and 2 are flowcharts of methods 100 and 200, respectively, for detecting design defects in accordance with embodiments of the present disclosure, FIG. 3 illustrates measurement of the topography of a wafer 310 and a chip 320 and the provision of design data 330 of the chip in accordance with an embodiment of the present disclosure, FIG. 4 illustrates calculation of a scanner moving average map 440 from topography data of the wafer in accordance with another embodiment of the present disclosure, FIG. 5 illustrates a topography map 510 across the wafer and a scanner defocus map 520 across the wafer in accordance with embodiments of the present disclosure, and FIG. 6 illustrates enlarged views and/or enhanced inspection of detected hotspot regions in accordance with embodiments of the present disclosure.

Method 100 includes receiving design data of an integrated circuit (IC) on a wafer at block 102, and measuring wafer topography across the wafer to obtain topography data at block 104. As noted above, FIG. 3 illustrates measurement of the topography of a wafer 310 and a chip 320 and the provision of design data 330 of the chip in accordance with an embodiment of the present disclosure.

Method 100 further includes calculating a scanner moving average from the topography data and the design data to provide a scanner defocus map across the wafer at block 106. As noted above, FIG. 4 illustrates calculation of a scanner moving average 440 from topography data 410 of the wafer in accordance with another embodiment of the present disclosure, and FIG. 5 illustrates a topography map 510 across the wafer and a scanner defocus map 520 across the wafer in accordance with embodiments of the present disclosure.

According to one aspect of the present disclosure, calculating the scanner moving average includes integrating scanner focus residuals along x and y directions across a wafer plane. In one example, topography data may be measured across an exposure field 410 (e.g., a 1 mm×1 mm grid), an exposure slit 420 (e.g., an 8 mm×26 mm slit) may be scanned (e.g., along 1 mm steps) across the exposure field or wafer, set points of topography data 432, scanner focus residual along the x-axis Rx 434, and scanner focus residual along the y-axis Ry 436 may be measured (e.g., at every 1 mm), and integrated to form scanner moving average map 440 across the wafer.

According to another aspect of the present disclosure, calculating the scanner moving average 440 follows the equation:

$$MA(x, y) = \frac{1}{s}\int_{-s/2}^{s/2} \{w(x, y) - [z(x, y+v) - vR_x(x, y+v) - xR_y(x, y+v)]\}dv$$

wherein x denotes the x-axis coordinate of the wafer plane,
y denotes the y-axis coordinate of the wafer plane,
z denotes an average wafer local height under a slit after least square (LSQ) plane fitting.
Rx denotes a scanner least square plane fit rotation angle about the x-axis within a slit,
Ry denotes a scanner least square plane fit rotation angle about the y-axis within a slit,
s denotes slit length along y axis (e.g. 8 mm),
w denotes wafer topography (z-height in nm) measured by level sensor, and v denotes a dummy variable of integration along slit in y direction.

Method 100 further includes determining a hotspot design defect from the scanner defocus map at block 108. As noted above, FIG. 6 illustrates enlarged views and/or enhanced inspection 630, 640 of detected hotspot regions of a chip 620 on a wafer 610 in accordance with embodiments of the present disclosure.

Method 200 illustrates an example of determining a hotspot design defect of method 100. In accordance with one embodiment, method 200 includes searching a library of hotspot defect patterns at block 202, detecting a hotspot defect pattern in the scanner defocus map at block 204, making a decision to either compensate or not for the hotspot design defect at decision block 206, filtering the detected hotspot defect pattern from the design data of the IC at block 208 if not compensating for the hotspot defect, and adjusting a scanner depth of focus at block 210 if compensating for the hotspot defect.

It should be noted that the operations of methods 100 and 200 may be rearranged or otherwise modified within the scope of the various aspects. It is further noted that additional processes may be provided before, during, and after the methods 100 and 200, and that some other processes may only be briefly described herein. Thus, other implementations are possible within the scope of the various aspects described herein.

According to another aspect of the present disclosure, determining the hotspot design defect may include detecting a hotspot defect pattern in the scanner defocus map as noted above with respect to method 200. The hotspot defect pattern may be from a searchable library of hotspot defect patterns.

According to another aspect of the present disclosure, receiving design data of an integrated circuit (IC) on a wafer, measuring topography of the IC across the wafer to obtain topography data, calculating a scanner moving average from the topography data and the design data to provide a scanner defocus map across the wafer, and/or determining a hotspot design defect from the scanner defocus map is performed prior to photolithography processing.

Inspecting the wafer inside or outside a process window may include inspecting the wafer inside or outside an active area or critical area of the wafer. Furthermore, inspecting the wafer outside the process window may include inspecting the wafer inside a dummy area of the wafer, which is outside an active area or critical area of the wafer.

In one embodiment, the term "inspecting" or "inspection" as used herein may be used interchangeably or alternatively with "measuring" or "measurement" to refer to enhanced defect inspection or defect review or full-wafer/chip topography measurement. In one example, topography measurement, enhanced defect inspection, or defect review may include metrology to measure one or more characteristics of the wafer, such as a dimension (e.g., topography, line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

In another example, enhanced defect inspection or defect review may involve generating additional information about defects at a higher resolution using either a high magnification optical system or a scanning electron microscope (SEM). The higher resolution data for the defects generated by defect review is more suitable for determining attributes of the defects such as profile, roughness, more accurate size information, etc. Defect analysis may also be performed using a system such as an electron dispersive x-ray spectroscopy (EDS) system. Such defect analysis may be performed to determine information such as composition of the defects. Attributes of the defects determined by inspection, review, analysis, or some combination thereof can be used to identity the type of the defect (i.e., defect classification) and possibly a root cause of the defects. This information can then be used to monitor and alter one or more parameters of one or more semiconductor fabrication processes to reduce or eliminate the defects. For example, if hotspot design defects are detected from the topography measurement correlated to the design data, a scanner depth of focus may be adjusted to compensate for the detected hotspot. A defect review tool may be used to revisit defects detected on a wafer or reticle and to examine the defects further in some manner either automatically or manually. In one example, a metrology tool for measuring topography across the wafer and the chip is available from Zygo Corporation of Middlefield, Connecticut.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices such as integrated circuits (ICs) may be formed on a wafer, and the term wafer as used herein is intended to encompass a wafer on which any type of device known in the art is being fabricated.

Although embodiments are described herein with respect to wafers, it is to be understood that the embodiments may be used for another specimen such as a reticle, which may also be commonly referred to as a mask or a photomask. Many different types of reticles are known in the art, and the terms "reticle", "mask", and "photomask" as used herein are intended to encompass all types of reticles known in the art.

The term "design data" as used herein generally refers to the physical design (layout) of an IC and data derived from the physical design through complex simulation or simple geometric and Boolean operations. Examples of design data include a partial or complete pre-existing design file or mask data set (e.g., GDS, GDS2, GDS2 derivative, or equivalent file or data type). In addition, an image of a reticle acquired by a reticle inspection system and/or derivatives thereof can be used as a "proxy" or "proxies" for the design data. Such a reticle image or a derivative thereof can serve as a substitute for the design layout in any embodiments described herein that use design data. The design data may include any other design data or design data proxies described in U.S. Pat. No. 6,886,153 to Bevis, U.S. Pat. No. 7,570,796 to Zafar et al., U.S. Pat. No. 7,676,077 to Kulkarni et al., and U.S. Pat. No. 7,711,514 to Park et al., both of which are incorporated by reference as if fully set forth herein.

In general, the embodiments described herein may further include generating a metrology sampling plan including measuring wafer topography correlated to design data prior to photolithograpy processing, and more particularly may further include a computer-implemented method for generating a metrology sampling plan.

In one embodiment, defects detected on the wafer may include pattern defects. The pattern defects may include systematic defects. Pattern or systematic defects may be identified and separated from other defects detected on the wafer (e.g., random defects and/or nuisance defects) as described in the patents by Kulkarni et al. and Zafar et al., which are incorporated by reference above. However, the defects may include any other defects known in the art (e.g., random defects) and may be generally referred to as hotspots throughout this document. In addition, the defects may include all of the defects detected on the wafer, which may include different types of defects (e.g., systematic defects and random defects), and which will vary depending on the results of the inspection of the wafer.

A method for detecting design defects may include performing defect inspection using sample wafers. In this manner, the method may include generating results of inspection of the wafer by performing inspection of the wafer (e.g., by performing one or more scans of the wafer using an inspection system described herein or another suitable inspection system). However, the embodiments described herein may not include performing inspection of the wafer. For example, the embodiments described herein may include acquiring the results of inspection of the wafer from an inspection system that performed the inspection or from a storage medium (e.g., a storage medium of the inspection system, a fab database, etc.) in which the inspection system stored the results of the inspection of the wafer.

A method for detecting design defects may include defining a defect pattern from inspection data. A population of defects may be located in a predetermined design pattern on a wafer. In one embodiment, the predetermined design pattern in which the population of defects is located is formed at multiple locations on the wafer. In another embodiment, the predetermined design pattern includes only a portion of an entire design patterned on the wafer. For example, a die formed on the wafer may include a number of different patterns, and the predetermined design pattern may include one specific pattern that forms only a portion of a die formed on the wafer. Therefore, the predetermined design pattern may be formed in each die formed on the wafer. In this manner, at least one instance of the predetermined design pattern may be formed in each die on the wafer. In addition, each die may include more than one instance of the predetermined design pattern (e.g., depending on the repetition of the predetermined design pattern in the die). Therefore, the predetermined design pattern may be formed at multiple instances in a die and in more than one die formed on the wafer.

In another embodiment, a method for detecting design defects may include identifying the population of defects by overlaying results of inspection of the wafer with locations of the predetermined pattern on the wafer. The results of inspection of the wafer may be acquired using any suitable inspection process and any suitable inspection system such as those described herein. For example, the inspection results may be acquired using a BF inspection system, an electron beam based inspection system, or any other suitable inspection system known in the art. In this manner, the results of the inspection that may be used by the embodiments described herein may be generated by various inspection technologies including BF, dark field (DF), and electron beam inspection technologies. The inspection results may also include any information generated during inspection of the wafer or by an inspection system used to inspect the wafer. For example, the inspection results may include defect locations reported by the inspection system, defect sizes reported by the inspection system, images of the defects such as patch images generated by the inspection system, or any other output generated by the inspection system.

Overlaying the results of the inspection of the wafer with locations of the predetermined design pattern on the wafer may be performed in any suitable manner. For example, the method may include overlaying inspection results to pattern of interest templates. In one such example, the locations of the predetermined pattern on the wafer may be determined based on information about the location(s) of the predetermined pattern within the dies formed on the wafer, information about the locations of the dies formed on the wafer, etc. Therefore, the locations of the predetermined design pattern on the wafer may be overlaid with results of the inspection such as a map of the wafer or a die on the wafer that illustrates wafer topography or positions of the defects on the wafer or in the die. In this manner, defects that are located within the predetermined design pattern can be identified using the map on which the locations of the predetermined pattern are overlaid.

If such a topography or defects map is included in the results of the inspection of the wafer or generated by the embodiments described herein, the locations of the predetermined design pattern on the wafer may be overlaid on the topography or defects map, and defects that are located within the predetermined design pattern or that have locations that at least partially overlap with the locations of the predetermined design pattern can be identified in the map.

For example, the wafer topography or locations of the defects detected on the wafer may be reported by an inspection system and included in the results of the inspection. In addition, the locations of the predetermined pattern on the wafer may be determined as described above. Therefore, the wafer topography or locations of the defects on the wafer and the locations of the predetermined pattern on the wafer may be compared (e.g., by comparing the x and y coordinates for the defects to the x and y coordinates for the predetermined pattern), which may be performed in any suitable manner, and any defects that are located within the location of the predetermined pattern on the wafer may be identified and included in the population of defects.

A pattern search or pattern based matching for a defined defect pattern within the design data may be used to determine design defects in the scanner defocus map. For example, a defect pattern library may be created and patterns in the library may be matched to defect inspection results.

In some embodiments, identifying the hotspot design defects may include the use of statistical analysis of the one or more attributes of the population of defects. For example, by performing a descriptive statistical analysis among the detected population of defects using inspection attributes (e.g., size, contrast, polarity, etc.), atypical patterns can be identified for metrology such as CD measurement. In this manner, the embodiments described herein may use a statistical approach to analyze inspection attributes to identify abnormal sites on the wafer, which can be used to determine sampling sites (e.g., sites at which CD measurements should be performed).

In another embodiment, identifying the one or more individual defects that have one or more attributes that are abnormal includes statistical analysis of images of the individual defects. For example, statistical analysis may be performed on patch images (or scanning electron microscope (SEM) images) of the defects that fall into the POI template. The input parameters for the statistical analysis may include various defect attributes such as brightness, contrast, size, etc., which may be provided by the defect inspection system or determined by the embodiments as described further herein.

The present disclosure also includes generating an enhanced review/metrology sampling plan based on results of identifying the one or more individual defects that have one or more attributes that are abnormal such that one or more areas on the wafer in which the one or more identified individual defects are located are sampled during metrology. In this manner, the method includes generating a sampling plan for the areas on the wafer that is determined to be atypical. In addition, the method includes generating a metrology sampling procedure that takes into account defect inspection data that shows abnormality among various sites and design context. For example, as described further herein, inspection data such as BF inspection data can be used to identify abnormal (or outlier) sites on the wafer, and the metrology sampling plan can be generated such that measurements such as CD measurements are performed at these abnormal sites during metrology. In this manner, a CD sampling plan may be generated for sampling of the outliers.

The enhanced review/metrology sampling plan may be generated in any suitable format (such as a file format that can be used by a metrology system). In addition, the metrology sampling plan may be generated by creating a new metrology sampling plan that includes the one or more areas on the wafer in which the one or more identified individual defects are located as the areas to be sampled or altering an existing metrology sampling plan by changing the samples areas in the existing plan to the one or more areas on the wafer in which the one or more identified individual defects are located.

In another embodiment, generating the metrology sampling plan is performed dynamically. For example, the embodiments described herein can use defect inspection data to create dynamic sampling (e.g., for CD measurements). In particular, since the metrology sampling plans are generated as described herein based on results of inspection of the wafer, a metrology sampling plan can be generated for each wafer for which inspection results have been generated. In some embodiments, therefore, generating the metrology sampling plan is performed on a wafer-to-wafer basis. As such, the metrology sampling plans can be generated as described herein dynamically such that measurements can be performed at dynamically determined sampling locations.

In one embodiment, the metrology includes wafer topography metrology and CD metrology. However, the metrology may include any suitable metrology process, which may include performing any suitable measurements using any suitable metrology system. For example, the metrology process may include measuring CD using a scatterometry system. In another example, the metrology process may include measuring roughness using an atomic force microscope (AFM). In yet another example, the metrology process may include measuring profile of the defects using a scanning electron microscope (SEM). In addition, the metrology may include performing one or more different measurements of the defects using one or more measurement techniques. The methods described herein also may or may not include performing metrology of the wafer using the metrology sampling plan generated as described herein. For example, the metrology sampling plan may be used by the embodiments described herein or another system or method to perform metrology of the wafer.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method generates the metrology sampling plan, the method may include storing the metrology sampling plan in a metrology recipe in a storage medium. In addition, results or output of the embodiments described herein may be stored and accessed by a metrology system such as a CD SEM such that the metrology system can use the metrology sampling plan for metrology assuming that the output file can be understood by the metrology system. Furthermore, the results may be stored "permanently", "semi-permanently", temporarily, or for some period of time. For example, the storage medium may be random access memory (RAM), and the results may not necessarily persist indefinitely in the storage medium.

Each of the embodiments of the method described above may include any other step(s) of any other method(s) described herein. In addition, each of the embodiments of the method described above may be performed by any of the systems described herein.

Figure 7:
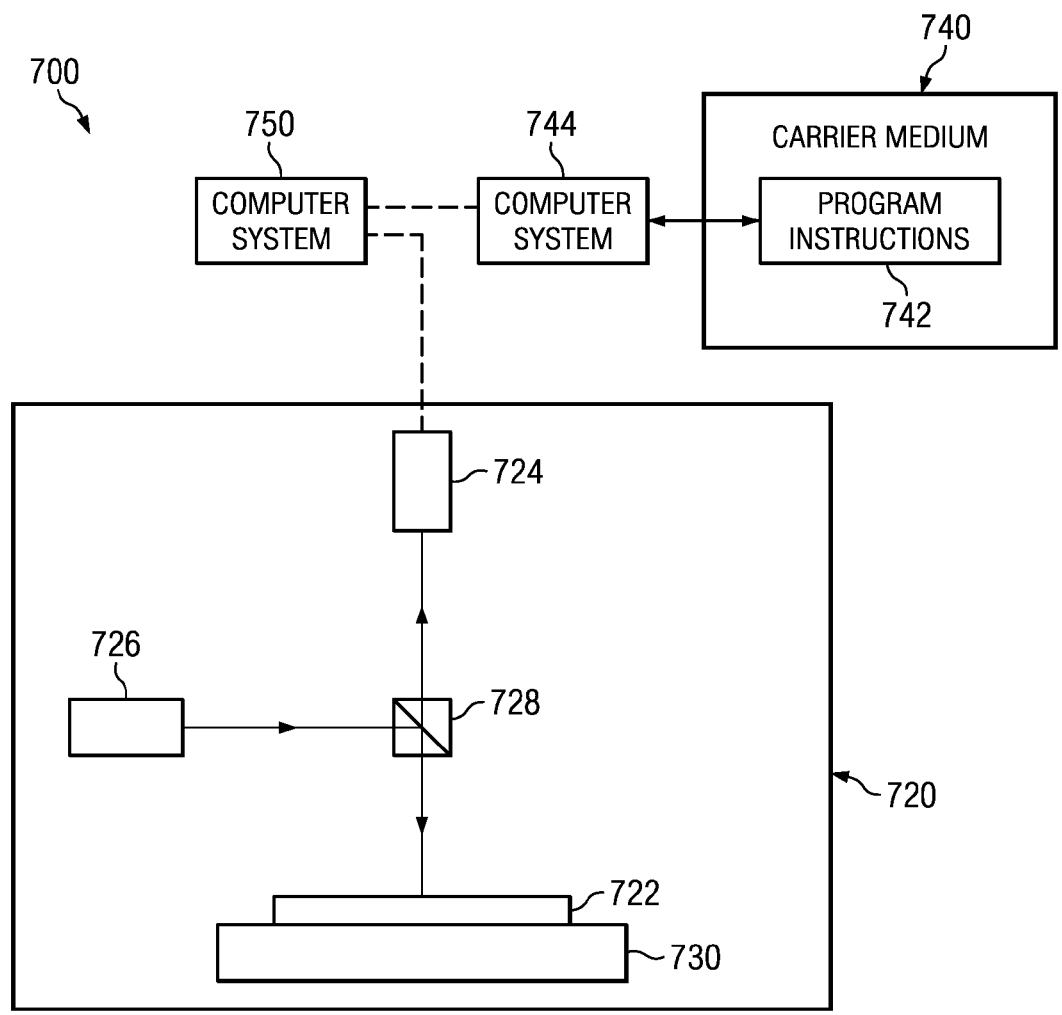
FIGS. 7-9 illustrate different systems for detecting design defects in accordance with embodiments of the present disclosure.
Figure 8:
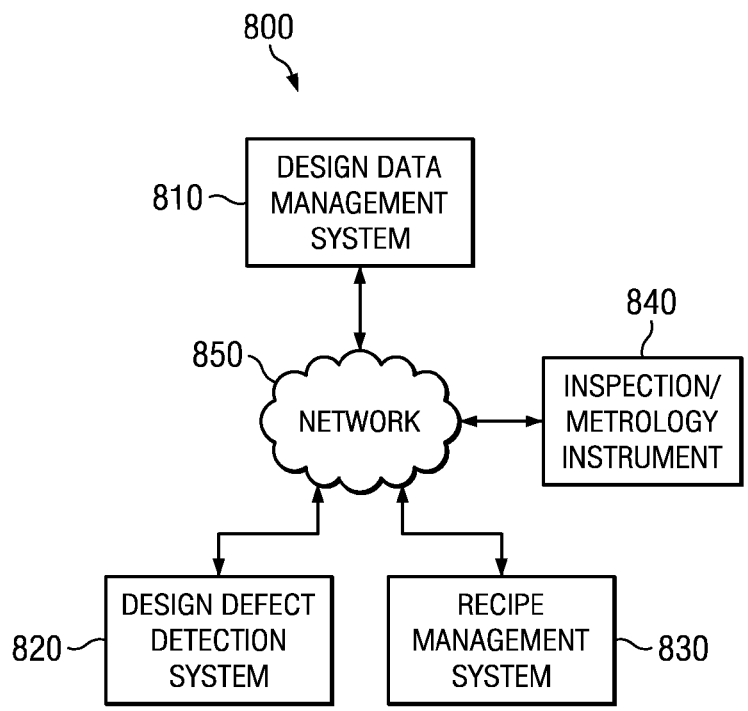
Figure 9:
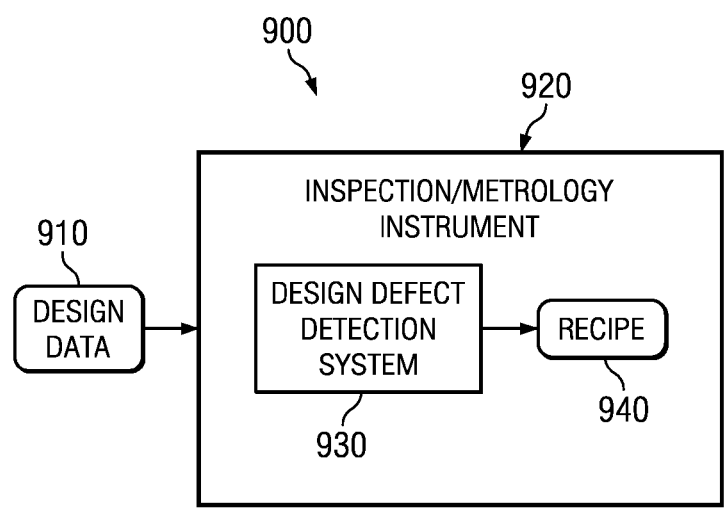

Referring now to FIGS. 7-9, different systems for detecting design defects are illustrated. FIG. 7 illustrates a system 700B including a carrier medium that includes program instructions executable on a computer system for performing a computer-implemented method for detecting design defects. In particular, a carrier medium 740 includes program instructions 742 executable on computer system 744 for performing a computer-implemented method.

The computer-implemented method includes obtaining first inspection data from inspecting a wafer outside a process window, defining a defect pattern from the inspection data, filtering defects from design data using a pattern search for the defined defect pattern within the design data, obtaining second inspection data from inspecting defects inside the process window with greater sensitivity than outside the process window, and determining design defects inside the process window. Generating the enhanced review/metrology sampling plan may be performed according to any of the embodiments described herein.

The computer-implemented method executable on the computer system by the program instructions may include any other step(s) of any other method(s) described herein. In addition, the carrier medium may be further configured as described herein.

Program instructions 742 implementing methods such as those described herein may be transmitted over or stored on carrier medium 740. The carrier medium may be a transmission medium such as a wire, cable, or wireless transmission link. The carrier medium may also be a storage medium such as a read-only memory, a random access memory, a magnetic or optical disk, or a magnetic tape.

Computer system 744 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

An additional embodiment relates to a system configured to generate a metrology sampling plan. The system includes an inspection system configured to detect defects on a wafer. For example, as shown in FIG. 7, the system includes inspection system 720. Inspection system 720 is configured to detect defects on wafer 722.

In one embodiment, inspection system 720 includes light source 726. Light source 726 may include any appropriate light source known in the art. Light source 726 may be configured to direct light to beam splitter 728. Beam splitter 728 may be configured to direct light from light source 726 to wafer 722 at a substantially normal angle of incidence. Beam splitter 728 may include any appropriate optical component known in the art.

Light reflected from wafer 722 may pass through beam splitter 728 to detector 724. Detector 724 may include any appropriate detector known in the art. Output generated by detector 724 may be used to detect defects on wafer 722. For example, computer system 750 may be configured to detect defects on wafer 722 using output generated by the detector. The computer system may use any method and/or algorithm known in the art to detect defects on the wafer. The computer system may be coupled to the detector in any suitable manner (e.g., by one or more transmission media indicated by the dotted line shown in FIG. 7, which may include any suitable transmission media known in the art) such that the computer system can receive the output generated by the detector. Furthermore, if the inspection system includes more than one detector (not shown), the computer system may be coupled to each detector as described above. Computer system 750 may be further configured as described herein. During inspection, wafer 722 may be disposed on stage 730. Stage 730 may include any appropriate mechanical and/or robotic assembly known in the art. The inspection system shown in FIG. 7 may also include any other suitable components (not shown) known in the art.

As shown in FIG. 7, the inspection system is configured to detect light specularly reflected from the wafer. In this manner, the inspection system shown in FIG. 7 is configured as a BF inspection system. However, the inspection system may be replaced by an inspection system configured as a DF inspection system, an edge contrast (EC) inspection system, an aperture mode inspection system, or any other optical inspection system known in the art. In addition, the inspection system may be configured to perform one or more inspection modes. For example, the inspection system shown in FIG. 7 may be configured to perform DF inspection by altering an angle of incidence at which the light is directed to the wafer and/or an angle at which light is collected from the wafer. In another example, the inspection system may be configured such that one or more optical components (not shown) such as apertures may be positioned in the illumination path and the collection path such that the inspection system can perform EC mode inspection and/or an aperture mode of inspection. Furthermore, the wafer inspection system described above may be replaced by a reticle inspection system, which may include any suitable reticle inspection system known in the art.

It is noted that FIG. 7 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In another embodiment, the optical inspection system shown in FIG. 7 may be replaced by an electron beam inspection system.

The system also includes computer system 744 configured to identify one or more individual defects that have one or more attributes that are abnormal from one or more attributes of a population of defects in which the individual defects are included. The population of defects is located in a predetermined pattern on the wafer. The computer system may be configured to identify the one or more individual defects according to any of the embodiments described herein. Computer system 744 is also configured to generate the metrology sampling plan based on the one or more identified individual defects such that one or more areas on the wafer in which the one or more identified individual defects are located are sampled during metrology. The computer system may be configured to generate the metrology sampling plan according to any of the embodiments described herein. Computer system 744 may be configured to perform any other step(s) of any of the method embodiment(s) described herein.

In embodiments of the system that include the inspection system, computer system 744 may be coupled to the inspection system in any manner known in the art. For example, computer system 744 may be coupled to computer system 750 of inspection system 720 such that the computer system can receive results of inspection generated by computer system 750. In addition, computer system 744 may receive any other output of the detector or computer system 750 such as image data and signals.

Computer system 744 described above may be configured as a stand-alone system that does not form part of a process, inspection, metrology, review, or other tool. In such an embodiment, computer system 744 may be configured to receive and/or acquire data or information from other systems (e.g., inspection results from an inspection system) by a transmission medium that may include "wired" and/or "wireless" portions. In this manner, the transmission medium may serve as a data link between the computer system and the other system. In addition, computer system 744 may send data to another system via the transmission medium. Such data may include, for example, a metrology sampling plan generated by the computer system.

Alternatively, computer system 744 may form part of the inspection system, metrology system, or other tool. For example, computer system 744 may be included in a metrology system. Therefore, the metrology system may be coupled to the inspection system by its computer system, and the computer system of the metrology system may be configured to generate the metrology sampling plan as described herein. In one such embodiment, the inspection system may include a BF inspection system such as those described herein, and the metrology system may include a defect review SEM that has CD measurement capability. In another example, computer system 750 may be configured as described above with respect to computer system 744. In this manner, the computer system included in the inspection system may be configured to identify the one or more individual defects as described above and to generate the metrology sampling plan as described above. In such embodiments, computer system 744 may or may not be included in the system.

The embodiments of the system shown in FIG. 7 may be further configured as described herein. In addition, the system may be configured to perform any other step(s) of any of the method embodiment(s) described herein.

FIG. 8 is a design driven inspection/metrology architecture including a network according to an embodiment of the present invention. Design data management system 810, design defects detection system 820, recipe management system 830, and inspection/metrology instrument 840 are operatively coupled via network 850. In one embodiment, network 850 is a local area network running a switched ethernet protocol. Other types of networks including metropolitan, wide area, or wireless networks may be used.

Design data management system 810 may be a file library of mask set data in one example. Design data management system 810 can also be a database or other appropriate data store. Design data management system 810 includes design data representing, for example, a plurality of layers of an integrated circuit layout, a plurality of devices, schematic data, layout verification data, and designer intent data. In addition to the data types just enumerated, one skilled in the art will appreciate that design data management system 810 can store or retrieve any type of data used in the design process.

Design defects detection system 820 may include a computer such as computer system 744 and/or 750 illustrated in FIG. 7, and interfaces with at least design data management system 810 and recipe management system 830. Defects detection system 820 retrieves and processes design data from design data management system 810. In one embodiment, design defects detection system 820 produces recipes that are stored in recipe management system 830.

Inspection/metrology instrument 840 retrieves recipes appropriate for a single test or suite of tests from recipe management system 830. One skilled in the art will appreciate that although a single inspection/metrology instrument is illustrated in FIG. 8, several such instruments can be coupled via network 850 or other networks (not shown).

Design data management system 810 enables "off-line" (i.e., not on a specific, physical inspection or measurement system) interaction with design data which improves the productivity of "on-line" in-fab inspection and measurement systems. The design driven data inspection/metrology is dramatically faster and more accurate because the operation is preferably software driven, thereby eliminating manual interaction with physical stages and the associated errors. A direct translation of the coordinates are selected and used at the "micro" level rather than a manual, macro-level interaction with trackballs, mouses, stages, display devices, etc. Moreover, in an embodiment, this process can be automated for specific layers (or content) of the design data (e.g., GDS2 file or equivalent data files or types) greatly simplifying setup and improving the productivity of all downstream process systems which may be dependent upon the results of these inspection and measurement systems.

The architecture illustrated in FIG. 8 provides several benefits. Recipe management system 830 performs central storage and/or delivery functions that make the availability, translation, and integration of these design data types more accessible to the inspection/metrology systems. Furthermore, a single setup session, including one to many design layers, allows identifying inspection areas and measurement points within the device for a wide variety of measurement and inspection systems-thereby streamlining the process for a variety of measurements simultaneously. Throughput (run rate) of the inspection/metrology device is improved by generally reducing the inspected or measured area to that which is of the highest value, thereby reducing the processing overhead (and run rate) of the inspection/metrology system. By reducing the data to only that which is directly relevant to a specific layer or layers, the quality and accuracy of the data is increased for the purpose of material disposition and predicting yield or eventual device performance.

FIG. 9 is a further block diagram of a design driven inspection/metrology system according to an embodiment of the present invention. In the illustrated embodiment, design data 910 is imported to inspection/metrology instrument 920. Design data 910 includes mask set data in one example. Among other functional units and data collection tools, inspection/metrology instrument 920 may comprise an integrated design defects detection system 930 and corresponding recipe 940. Design defects detection system 930 performs the particular analysis on design data 910 in conjunction with inspection data that is required to generate recipe 940 appropriate for inspection/metrology instrument 920, as described in the methods herein. That is, for a given inspection/metrology test, a particular subset of design data 910 may be relevant. For example, design data 910 preferably includes information relating to the multiple layers of the production process. Inspection/metrology instrument 920 can, for example, require information about regions of a particular layer of design data 910. Design defects detection system 930, therefore, performs the particular analysis required for inspection/metrology instrument 920. Design defects detection system 930 eliminates or reduces the need for manual instrument time, thereby improving the productivity and availability of the tool for "in-line", repetitive, unique, or sequenced "production", measurements, and other types of measurements supporting the engineering and production activities associated with a fabrication line.

Thus, the present disclosure provides for various embodiments. According to one embodiment, a method for detecting design defects is provided. The method includes receiving design data of an integrated circuit (IC) on a wafer, measuring wafer topography across the wafer to obtain topography data, calculating a scanner moving average from the topography data and the design data to provide a scanner defocus map across the wafer, and determining a hotspot design defect from the scanner defocus map.

In another embodiment, a computer readable storage medium is provided. The computer readable storage medium comprises computer readable instructions which when executed by a computer cause the computer to perform the operations of: receiving design data of an integrated circuit (IC) on a wafer; measuring wafer topography across the wafer to obtain topography data; calculating a scanner moving average from the topography data and the design data to provide a scanner defocus map across the wafer; and determining a hotspot design defect from the scanner defocus map.

In yet another embodiment, a system for detecting design defects is provided. The system includes an inspection tool configured to measure wafer topography across a wafer to obtain topography data, and a processor operably coupled to the inspection tool, the processor configured to perform the operations of: receiving design data of the IC on the wafer; calculating a scanner moving average from the topography data and the design data to provide a scanner defocus map across the wafer; and determining a hotspot design defect from the scanner defocus map.

Although embodiments of the present disclosure have been described in detail, those skilled in the art should understand that they may make various changes, substitutions and alterations herein without departing from the spirit and scope of the present disclosure. Accordingly, all such changes, substitutions and alterations are intended to be included within the scope of the present disclosure as defined in the following claims. In the claims, means-plus-function clauses are intended to cover the structures described herein as performing the recited function and not only structural equivalents, but also equivalent structures.

What is claimed is:

1. A method of detecting design defects, the method comprising:
   receiving design data of an integrated circuit (IC) on a wafer;
   measuring wafer topography across the wafer to obtain topography data;
   calculating a scanner moving average from the topography data and the design data to provide a scanner defocus map across the wafer; and
   determining a hotspot design defect from the scanner defocus map.

2. The method of claim 1, wherein calculating the scanner moving average includes integrating scanner focus residuals along x and y directions across a wafer plane.

3. The method of claim 1, wherein calculating the scanner moving average follows the equation:

$$MA(x, y) = \frac{1}{s}\int_{-s/2}^{s/2}\{w(x, y) - [z(x, y+v) - vR_x(x, y+v) - xR_y(x, y+v)]\}dv$$

wherein x denotes the x-axis coordinate of the wafer plane,
y denotes the y-axis coordinate of the wafer plane,
z denotes an average wafer local height under a slit after least square (LSQ) plane fitting.
Rx denotes a scanner least square plane fit rotation angle about the x-axis within a slit,
Ry denotes a scanner least square plane fit rotation angle about the y-axis within a slit,
s denotes slit length along y axis,
w denotes wafer topography (z-height) measured by level sensor, and
v denotes a dummy variable of integration along slit in y direction.

4. The method of claim 1, wherein determining the hotspot design defect includes detecting a hotspot defect pattern in the scanner defocus map.

5. The method of claim 4, wherein the hotspot defect pattern is from a library of hotspot defect patterns.

6. The method of claim 1, wherein determining the hotspot design defect is performed prior to photolithography processing.

7. The method of claim 1, further comprising:
   filtering the hotspot design defect from the design data.

8. A computer readable storage medium comprising computer readable instructions which when executed by a computer cause the computer to perform the operations of:
   receiving design data of an integrated circuit (IC) on a wafer;
   measuring wafer topography across the wafer to obtain topography data;
   calculating a scanner moving average from the topography data and the design data to provide a scanner defocus map across the wafer; and
   determining a hotspot design defect from the scanner defocus map.

9. The computer readable storage medium of claim 8, wherein calculating the scanner moving average includes integrating scanner focus residuals along x and y directions across a wafer plane.

10. The computer readable storage medium of claim 8, wherein calculating the scanner moving average follows the equation:

$$MA(x, y) = \frac{1}{s}\int_{-s/2}^{s/2}\{w(x, y) - [z(x, y+v) - vR_x(x, y+v) - xR_y(x, y+v)]\}dv$$

wherein x denotes the x-axis coordinate of the wafer plane,
y denotes the y-axis coordinate of the wafer plane,
z denotes an average wafer local height under a slit after least square (LSQ) plane fitting.
Rx denotes a scanner least square plane fit rotation angle about the x-axis within a slit,
Ry denotes a scanner least square plane fit rotation angle about the y-axis within a slit,
s denotes slit length along y axis,
w denotes wafer topography (z-height) measured by level sensor, and
v denotes a dummy variable of integration along slit in y direction.

11. The computer readable storage medium of claim 8, wherein determining the hotspot design defect includes detecting a hotspot defect pattern in the scanner defocus map.

12. The computer readable storage medium of claim 11, wherein the hotspot defect pattern is searched from a library of hotspot defect patterns.

13. The computer readable storage medium of claim 8, wherein determining the hotspot design defect is performed prior to photolithography processing.

14. The computer readable storage medium of claim 8, further comprising computer readable instructions which when executed by a computer cause the computer to perform the operation of either filtering the hotspot design defect from the design data or compensating for the hotspot design defect by adjusting a scanner depth of focus.

15. A system for detecting design defects, the system comprising:
   an inspection tool configured to measure wafer topography across a wafer to obtain topography data; and
   a processor operably coupled to the inspection tool, the processor configured to perform the operations of:
   receiving design data of the IC on the wafer;
   calculating a scanner moving average from the topography data and the design data to provide a scanner defocus map across the wafer; and
   determining a hotspot design defect from the scanner defocus map.

16. The system of claim 15, wherein the processor is configured to calculate the scanner moving average by integrating scanner focus residuals along x and y directions across a wafer plane.

17. The system of claim 15, wherein the processor is configured to calculate the scanner moving average following the equation:

$$MA(x, y) = \frac{1}{s}\int_{-s/2}^{s/2}\{w(x, y) - [z(x, y+v) - vR_x(x, y+v) - xR_y(x, y+v)]\}dv$$

wherein x denotes a function of an x-axis of the wafer plane,
y denotes a function of a y-axis of the wafer plane,
z denotes a function of a z-axis perpendicular to the wafer plane,
Rx denotes a scanner focus residual along the x-axis, Ry denotes a scanner focus residual along the y-axis, s denotes slit length along y-axis, w denotes wafer topography (z-height) measured by level sensor, and v denotes a dummy variable of integration along slit in y direction.

18. The system of claim 15, wherein the processor is configured to determine the hotspot design defect prior to photolithography processing by detecting a hotspot defect pattern in the scanner defocus map, the hotspot defect pattern stored in a library of hotspot defect patterns.

19. The system of claim 15, wherein the processor is further configured to perform the operation of either filtering the hotspot design defect from the design data or compensating for the hotspot design defect by adjusting a scanner depth of focus.

* * * * *